US005269324A

United States Patent [19]

Butterfield

[11] Patent Number: 5,269,324

[45] Date of Patent: Dec. 14, 1993

[54] PATIENT LIFTING HARNESS AND METHOD OF USE

[76] Inventor: Ida M. Butterfield, 1026 Buchanan, Yuba City, Calif. 95991

[21] Appl. No.: 821,476

[22] Filed: Jan. 14, 1992

Related U.S. Application Data

[62] Division of Ser. No. 427,300, Oct. 26, 1989.

[51] Int. Cl.[5] .......................... A61F 5/37; A61B 19/00

[52] U.S. Cl. ...................................... 128/875; 128/898

[58] Field of Search ................. 128/869, 870, 873, 78, 128/874, 875, 84 C, 70, 72; 5/61, 81 R, 82 R, 424, 484, 485, 482, 460, 490, 501, 508; 2/45; 294/140, 149, 150, 153, 156, 157; 119/96

[56] References Cited

U.S. PATENT DOCUMENTS

| | | | |
|---|---|---|---|
| 2,212,746 | 8/1940 | Nunn | 119/96 |
| 2,568,304 | 9/1951 | Schoenbrun | 119/96 |
| 2,758,769 | 8/1956 | Nunn | 119/96 |
| 2,812,123 | 11/1957 | Girton | 224/150 |
| 3,458,878 | 8/1969 | Combs | 5/81 R |
| 3,884,225 | 5/1975 | Witter | 128/869 |
| 3,889,668 | 6/1975 | Ochs | 128/870 |
| 4,569,095 | 2/1986 | Holling | 5/82 R |
| 4,675,925 | 6/1987 | Littleton | 5/61 |
| 4,759,311 | 7/1988 | Boyle | 119/96 |
| 4,793,008 | 12/1988 | Johansson | 5/81 R |

*Primary Examiner*—Michael Brown
*Attorney, Agent, or Firm*—James M. Ritchey

[57] ABSTRACT

A device for raising a patient's upper body off the surface of an underlying support to insert a chest board between the back of the patient and the underlying support is disclosed comprising an adjustable body belt, attached shoulder strap, and associated handle. The belt is fitted around the patient's upper body, encircling the torso and arms. The shoulder strap and handle, with the shoulder strap running from the belt along the patient's back and over the patient's shoulder, provides the handle for grasping and easily raising the patient's upper body off the underlying surface.

8 Claims, 2 Drawing Sheets

PATIENT LIFTING HARNESS AND METHOD OF USE

This is a divisional of copending application Ser. No. 07/427,300 filed on 10-26-89.

BACKGROUND OF THE INVENTION

1. Field of the Invention

This invention relates to a device for raising a patient's upper body or torso off the surface of an underlying support so that a chest board may be inserted between the back of the patient and the underlying support. More particularly, with the patient's back against the underlying support surface, a combination adjustable belt and attached shoulder strap is fitted around the patient's upper body, encircling the torso and arms. The shoulder strap, coming from the belt and up along the patient's back and over a shoulder, provides a leverage means for easily raising the upper body off the underlying surface.

2. Description of the Background Art

Traditionally, to insert a chest board (an essentially rigid board that aids in insulating a patient from a supporting surface and provides a firm platform on which to perform CPR or similar procedures to the patient's exposed chest area) between a patient's back and an underlying supporting surface required an unsuitable and often dangerous amount of critical time. A medical staff member needed to grasp the patient and often struggle (especially if the patient was heavy and the staff member physically small) to lift the patient and then push the board into position. No suitable mechanical aids were available to assist the staff member in this difficult lifting and positioning process. Various harness devices exist for restraining or moving a person, but these prior art devices require ready access to the wearer's back region for fitting and usually demand the wearer's arms fit through small opening, neither of which are practical for a critically ill and possibly heavy patient.

U.S. Pat. No. 1,711,864 discloses an harness for guiding and restraining children. This harness requires a fitting for a particular child and fastens across the back region of the child.

Related in U.S. Pat. No. 2,212,746 is a safety harness for children which, like '864 above, fastens in the back region of a child. This device is used to restrain a child and may be secured to holding objects in various ways.

An additional child restraining device is disclosed in U.S. Pat. No. 2,568,304. Like the two harnesses above, '864 and '746, this restrainer fits over the shoulders of a child, with the child's arms fitted through encircling straps, and is engineered to prevent forward motion of the child. Lifting the restraining strap vertically up would result in the waste bands coming free.

U.S. Pat. No. 2,900,976 presents devices adapted for assisting paralyzed or hemiplegic persons. A limb is encircled by a band or sling and is leveraged into various positions by a flexible cord fastened to an handle and assisted by a pulley mechanism.

A device for instructing a person to swim is disclosed in U.S. Pat. No. 2,956,541. A loop harness fits around the arms of the person learning to swim. A resilient handle piece is fitted to the harness to permit an instructor to hold a potential swimmer in a proper position for swimming. As with the harnesses above, '864, '746, and '304, there must be ready access to the wearer's back area for fitting the wearer with the device.

Disclosed in U.S. Pat. No. 2,758,769 is a safety belt or harness for children to be used when a child is riding in a moving vehicle. A leash runs from a seat anchor to the back of a harness that is looped over the child's arms.

U.S. Pat. No. 3,669,107 presents a lap cover and restrainer that incorporates, as the lap cover, a bag-like enclosure that fits over a user's legs. For securing the user within the bag-like enclosure and to a supporting wheelchair, straps are associated with the bag. An upper body harness runs from the top of the bag-like enclosure and over a user's shoulder's and is anchored to the handle grips of the wheelchair.

An ambulatory support and guide strap is delineated is in U.S. Pat. No. 4,396,013. The device is positioned about the midsection of a wearer and is basically an adjustable belt with a pair of closely fitted handles. An attendant, standing behind the wearer, would grab the handles and assist the wearer by giving additional support and guidance during movement.

A device for manipulating a bedridden patient is revealed in U.S. Pat. No. 4,675,925. A flexible pliant sheet with tie straps and handles is fitted under a patient and is employed to turn the patient.

U.S. Pat. No. 4,793,008 discloses both a method of transferring a patient and mats used in the process. Two elongated transfer mats, each having a strap and an handle at each end, are fitted, without moving the patient, under the patient's shoulders and buttocks. The straps are secured from the mats, over the patient and the handles used to lift, pull, or turn the patient.

SUMMARY OF THE INVENTION

An object of the present invention is to provide a device for quickly raising a patient's upper body off the surface of an underlying support to permit a chest board to slide between the back of the patient and the support surface.

Another object of the present invention is to produce an inexpensive, compact, and easily stored means for raising a patient's upper body off the surface of an underlying support.

An additional object of the present invention is to create a lifting aid that permits a single individual to lift the upper body of an heavy patient far enough above a supporting surface to be able to slide a chest board between the patient and the supporting surface.

Yet another object of the present invention is to furnish a patient lifting device that may be fitted rapidly to a patient that is lying back down on a supporting surface without requiring access to the patient's back area.

The subject invention, a lifting harness, comprises an adjustable upper body belt secured to a lifting shoulder strap having an handle. The belt having two end regions is equipped with coupling means to permit the user to reversibly mate the end regions to each other to generate a linked structure (usually of approximately circular or oblong shape) of adjustable perimeter size. The lifting shoulder strap having a strap end domain at each of its two ends is attached via one of the strap end domains to the belt proximate the midpoint of the belt, between the belt end regions. Attached at the second strap end domain is an handle.

A user of the subject device positions a patient so that the patient's back is against the surface of a supporting structure, floor, or earth. The belt is slipped under the upper body of the patient's body and the coupling means mated over the patient's exposed chest area or arms to produce a securely linked and fitted encircling belt harness that surrounds the patient's upper body, including the arms. Since the coupling means links over the chest area or arms of the patient, access to the patient's back area is not required in fitting the harness, thus minimizing the need of moving the patient. The lifting shoulder strap runs from the belt attachment point under the patient and past a shoulder to expose the associated handle. By grasping the handle and pulling in a generally upward direction, a user has the necessary leverage to raise a patient's upper body off the underlying surface. Once raised, the user slips a chest board, or equivalent device, under the patient and lowers the patient on the chest board for further medical treatment.

Other objects, advantages, and novel features of the present invention will become apparent from the detailed description that follows, when considered in conjunction with the associated drawings.

DESCRIPTION OF THE PREFERRED EMBODIMENT

Figure 1:
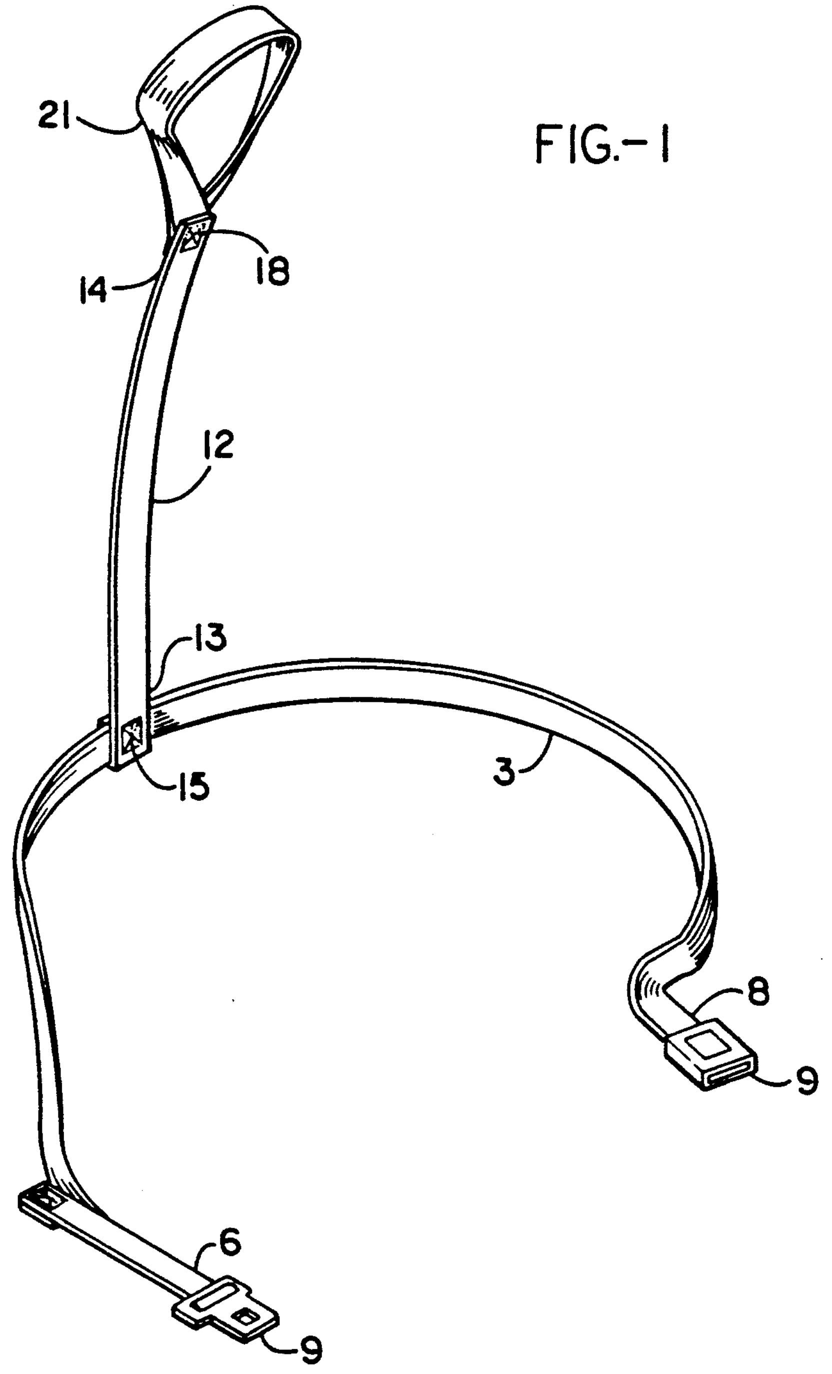
FIG. 1 is a perspective illustration of the subject lifting device.
Figure 2:
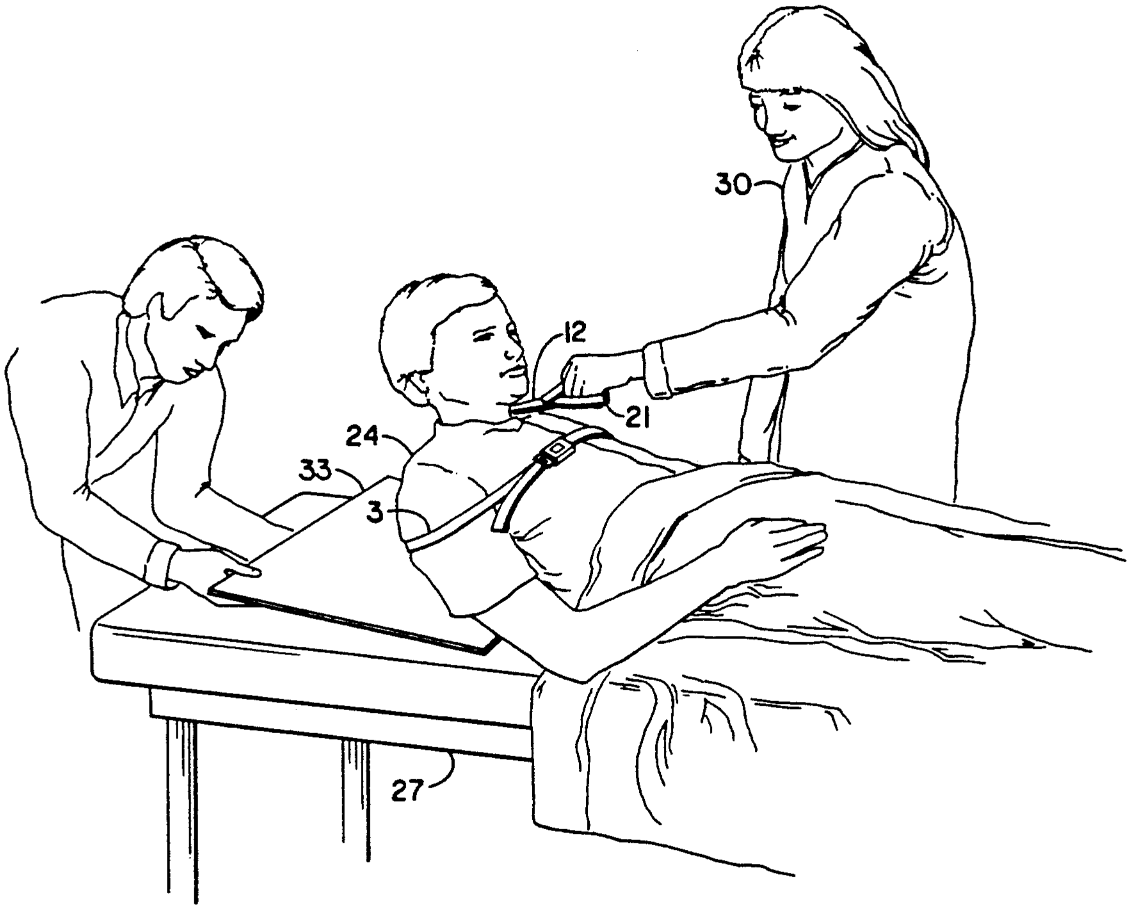
FIG. 2 is a perspective illustration of the subject lifting device being employed by a user on a patient to lift the patient's upper body off the underlying surface.

Referring now to FIGS. 1 and 2, there is shown a preferred embodiment of a patient lifting harness 1 of the subject invention. This device is for raising the upper body of a patient off the surface of an underlying support to permit the insertion of a chest board between the patient's back and the surface of the underlying support.

The subject invention, a patient lifting harness 1, as illustrated in particular in FIG. 1, comprises a body belt 3 having first 6 and second 8 end regions. The belt 3 is a band-like strip preferably of flattened and elongated rectangular proportions constructed from a sturdy material capable of withstanding the forces exerted by the heaviest patient. Suitable sturdy materials are woven or braided nylon or similar polymer, cloth, leather, or equivalent substances. Although the body belt 3 may be of any cross-sectional area, the flattened form is preferred. This flattened form permits a user to slip the belt 3 easily under the back of a reclining patient without the need of having free access to the patient's back area.

For adjustably fastening and fitting the body belt 3 about the upper body of a patient, around the upper portion of the torso, including the shoulder area of the arms, coupling means 9 are associated with the first 6 and second 8 belt end regions. The coupling means 9 forms a reversible mating link between the two belt end regions 6 and 8. The coupling means 9 serves to secure the belt 3 about a patient to form a reversibly linked structure (usually of approximately circular or oblong shape) of adjustable perimeter size. To facilitate a rapid fitting the coupling means 9 is readily adjustable to fit the physical size of the patient. As shown in FIGS. 1 and 2, the coupling means 9 is (as one depicted exemplary embodiment) a seatbelt-like latch with mating male and female components, one associated with each end region 6 and 8. These mating components are positioned, relative to the belt 3 and the patient, to mate on the easily accessible chest or side areas of the patient. As with a typical seat-belt in an airplane, the latch components are mated and the appropriate end of the belt 3 drawn tight to fit around the patient. In addition to the depicted seatbelt-like coupling means 9, other functionally equivalent coupling means may be employed, including a Velcro$^R$ mating pair, snaps, hooks and eyes, and like devices associated with the belt end regions 6 and 8. In particular, for a Velcro$^R$ mating pair having two members, each belt end region 6 and 8 is attached to one of the mating members. The length of the Velcro$^R$ mating members is sufficient to allow the user to adjust the belt 3 to fit around the patient.

A shoulder strap 12 terminating in first 13 and second 14 strap end domains is attached to the belt 3 via the first strap end domain 13. As with the belt 3, the shoulder strap 12 is preferably a flattened and elongated rectangular band of sturdy material of sufficient structural strength to easily withstand the weight of the heaviest patient. The shoulder strap 12 is connected to the belt 3 at a belt attachment point 15. Although other angles are contemplated to be within the realm of this disclosure, the angle between the belt 3 and the shoulder strap 12 long axes is approximately 90°, thereby generating a T-like attachment. The belt attachment point 15 is between the first 6 and second 8 belt end regions, preferably proximate the long axis midpoint of the belt 3. The length of the shoulder strap 12 is variable, usually between two and five feet and preferably about two to three feet.

Attached via the second strap end domain 14 at an handle attachment point 18 is an handle 21. As long as the handle 21 may be grasped quickly and easily by a user of the subject device, this handle 21 may be of varied structural design. Pictured in FIGS. 1 and 2 is a preferred strap-like loop handle 21 that is strong and readily grasped, in addition to being economical to produce.

Materials like those used to produce the belt 3 are appropriate for fabricating the shoulder strap 12 and handle 21. To attach the shoulder strap 12, standard methods are employed such as stitching, riveting, glueing, heating, braiding, or equivalent procedures.

FIG. 2 illustrates the subject device being used to lift the upper body of a patient 24 off the surface of an underlying support 27 (the support being a bed, crash cart, table, floor, ground, and the like). If the patient is situated with their back not in contact with the surface of the underlying support, the patient is positioned to have their back in contact with the surface of the underlying support. The belt 3 of the patient lifting harness is forced beneath the patient 24 for fitting. The belt 3 is forced under the patient's body at a body location proximate the patient's shoulders. Once the patient 24 has the belt 3 positioned under their back, the harness 1, specifically the belt 3, is fastened about the outer portion of the body to encircle the patient's upper body proximate the shoulders. The fastened belt 3 is adjusted by tightening or loosening the coupling means.

A medical staff member 30 (e.g., a nurse, technician, physician, or similar individual), grasps the handle 21 and leverages the patient 24 into a partially raised position by exerting a pulling force strong enough to raise the patient's upper body sufficiently off the underlying surface to insert a chest board 33. Since a typical chest board 33 is approximately an inch thick, the height the upper body is raised above the underlying surface need not be great. Either a lone staff member 30 or a staff member with assistants (one assistant being shown in FIG. 2) inserts a chest board 33 beneath the patient. The patient 24 is lowered by easing the pulling force on the lifting harness 1, specifically the handle 21. The harness 1 is removed either before of after medical treatment.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope fo the appended claims.

What is claimed is:

1. A method for raising the upper body of a patient off the surface of an underlying support to permit sliding a chest board between the patient's back and the surface of the underlying support, comprising the steps of:

a) forcing a patient lifting harness under a patient's body at a body location proximate said patient's shoulders;

b) fastening said lifting harness about the outer portion of said patient's body to encircle said patient's upper body proximate said patient'shoulders;

c) lifting said patient's upper body by exerting a pulling force on said lifting harness;

d) sliding a chest board under said patient's upper body between said patient's back and the surface of said underlying support; and e) lowering said patient by easing the pulling force on said lifting harness, said harness comprising a body belt terminating in first and second end regions; coupling means for reversible mating associated with said first and second body belt end regions, wherein when mated by said coupling means, said first and second body belt end regions form a reversibly linked structure of adjustable perimeter size encircling said patient's upper body proximate said patient's shoulder; a shoulder strap terminating in first and second end domains, wherein said shoulder strap first end domain is attached to said body belt between said body belt first and second end regions; and a handle formed into a loop for grasping to exert a pulling force attached to said shoulder strap second end domain, wherein said shoulder strap runs from said body belt along said patient's back to extend away from said patient, proximate said patient's shoulder, to permit grasping of said handle.

2. A method for raising the upper body of a patient according to claim 1, further comprising the initial step of positioning the back of said patient to contact the surface of said underlying support.

3. A method for raising the upper body of a patient according to claim 1, further comprising the step of removing said lifting harness from said patient.

4. A method for raising the upper body of a patient according to claim 1, wherein said coupling means is an adjustable seatbelt-like latch with male and female mating components, one of said components associated with each of said belt end regions.

5. A method for raising the upper body of a patient sufficiently above the surface of an underlying support to permit sliding a chest board between the patient's back and the surface of the underlying support, comprising the steps of:

a) forcing a patient lifting harness under a patient's body at a location proximate said patient's shoulders, wherein said lifting harness comprises a body belt terminating in first and second end regions, coupling means for reversible mating associated with said first and second body belt end regions, wherein when mated by said coupling means, said first and second body belt end regions form a reversibly linked structure of adjustable perimeter size, a shoulder strap terminating in first and second end domains, wherein said shoulder strap first end domain is attached to said body belt between said body belt first and second end regions, and an handle attached to said shoulder strap second end domain;

b) fastening said coupling means of said lifting harness about the outer portion of said patient's body to encircle said patient's upper body proximate said patient's shoulders;

c) positioning said shoulder strap to run from said body belt by said patient's back and to extend past said patient's shoulder;

d) lifting said patient's upper body by exerting a pulling force on said lifting harness by grasping said handle and pulling;

e) sliding a chest board under said patient's upper body between said patient's back and the surface of said underlying support; and f) lowering said patient by easing the pulling force on said lifting harness handle.

6. A method for raising the upper body of a patient according to claim 5, further comprising the initial step of positioning the back of said patient to contact the surface of said underlying support.

7. A method for raising the upper body of a patient according to claim 5, further comprising the step of removing said lifting harness from said patient by releasing said coupling means and slipping said body belt and said shoulder strap from under said patient.

8. A method for raising the upper body of a patient according to claim 5, wherein said coupling means is an adjustable seatbelt-like latch with male and female mating components, one of said components associated with each of said belt end regions.

* * * * *